United States Patent [19]

Hamanaka et al.

[11] 4,093,518
[45] June 6, 1978

[54] STIRRED GAS BUBBLE FERMENTER

[75] Inventors: Michito Hamanaka; Toshio Sano; Noriharu Kumura, all of Sodegaura, Japan

[73] Assignee: Idemitsu Kosan Company Limited, Tokyo, Japan

[21] Appl. No.: 762,422

[22] Filed: Jan. 25, 1977

[30] Foreign Application Priority Data

Feb. 4, 1976 Japan .................................. 51-10413

[51] Int. Cl.² ............................ C12B 1/12; C12B 1/18
[52] U.S. Cl. .................................... 195/142; 195/143; 55/178
[58] Field of Search ................ 195/142, 143; 252/361; 55/178

[56] References Cited

U.S. PATENT DOCUMENTS

| 3,231,251 | 1/1966 | Scheibel ................................... 55/178 |
| 3,747,304 | 7/1973 | Elmer et al. ............................ 55/178 |
| 3,847,748 | 11/1974 | Gibson et al. ......................... 195/142 |

*Primary Examiner*—Alvin E. Tanenholtz
*Attorney, Agent, or Firm*—Flynn & Frishauf

[57] ABSTRACT

A stirred gas bubble fermenter is provided with a cooler outside the fermenter which is coupled to the fermenter through an overflow exit. An overflow weir is connected to the inner wall of the fermenter below the overflow exit and extends at least in the upward direction of the fermenter. In a preferred embodiment, the overflow weir extends above the upper extremity of the overflow exit. The fermenter may further be provided with a guide plate arranged between at least a portion of the overflow weir and at least a portion of the overflow exit in order to more efficiently separate bubbles from a culture broth in the fermenter.

19 Claims, 10 Drawing Figures

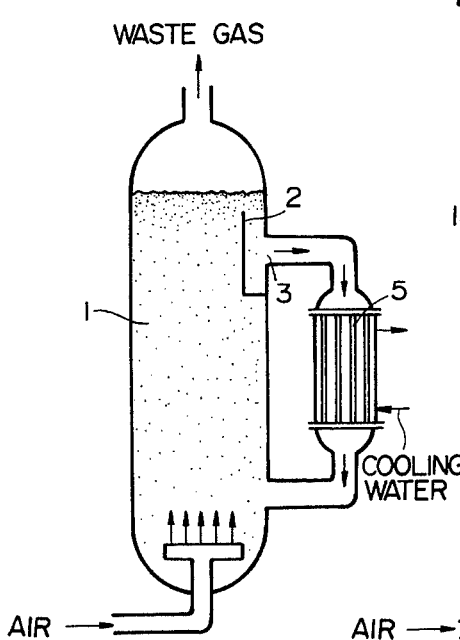 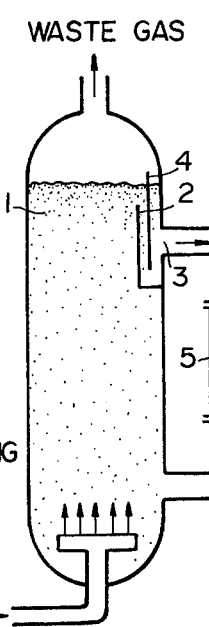 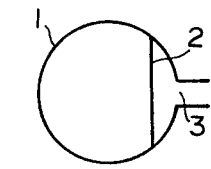 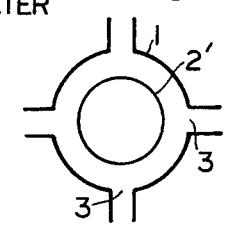
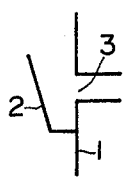 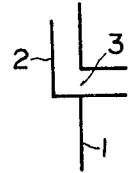 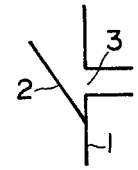 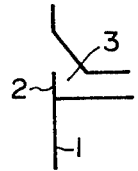
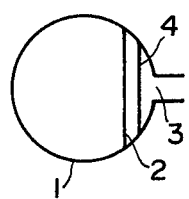 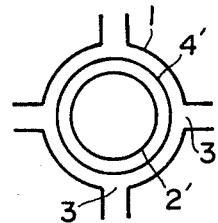

STIRRED GAS BUBBLE FERMENTER

FIELD OF THE INVENTION

The present invention relates to a stirred gas bubble fermenter provided with a cooler outside the fermenter. More particularly, it relates to a fermenter in which bubbles can be separated from a culture broth passed from the said fermenter to a cooler.

BACKGROUND OF THE INVENTION

In the method for culturing microorganisms such as yeast, bacteria, etc., under aerobic conditions to produce microbial cells and for producing useful substances such as antibiotics, amino acids, alcohols, etc., research and development was made about the measures for providing oxygen and for cooling culture broth heated during a fermentation process, etc., in both batch and continuous fermentation systems for the purpose of improving fermentation efficiency. For instance, a method for controlling the temperature of a culture broth by providing a cooling tube inside the fermenter is known. However, the diffusion efficiency of air provided in the fermenter into the culture broth is lowered in this method and, in addition, it has also the defect that the effective area inside the fermenter is reduced. Therefore, a fermentation process using a stirred gas bubble fermenter provided with a cooler and a device for eliminating bubbles outside the fermenter has also been proposed (ex. Japanese Patent Publication Gazette No. 26040/1964).

By way of illustration, in controlling a culture broth to an appropriate temperature by cooling it, it is necessary to remove bubbles in the culture broth passed into a cooler as much as possible in order to obtain a good cooling effect.

SUMMARY OF THE INVENTION

We have studied conditions for culturing microorganisms with a stirred gas bubble fermenter. As a result, we have found that the aforesaid problem can be solved by providing a relatively small-scale weir of simple structure inside the fermenter.

In accordance with the present invention, in a stirred gas bubble fermenter, bubbles are separated from a culture broth passed from the fermenter to a cooler by providing an overflow weir extended from the inner wall of the fermenter below the overflow exit to the upper direction of the fermenter. In addition, the present invention includes a fermenter provided with a guide plate between the aforesaid overflow weir and overflow exit in order to separate bubbles from the culture broth more efficiently.

BRIEF EXPLANATION OF THE FIGURES

FIGS. 1 and 2 illustrate typical embodiments of fermenters of the present invention.

FIG. 3 is a transverse section of the fermenter of FIG. 1.

FIG. 4 is a transverse section of a modification of the fermenter of FIG. 1.

FIGS. 5-8 illustrate various types of overflow weirs which may be provided.

FIG. 9 is a transverse section of the fermenter of FIG. 2.

FIG. 10 is a transverse section of a modification of the fermenter of FIG. 2.

In the Figures, reference numerals 1, 2, 3, 4 and 5, respectively, denote fermenter, overflow weir, overflow exit, guide plate and cooler.

EMBODIMENTS OF THE INVENTION

Referring to FIG. 1, overflow weir 2 is provided inside fermenter 1. Overflow weir 2 comprises a first section which extends horizontally from the inner wall of fermenter 1 below overflow exit 3, and a second vertical section which extends upwardly from the first horizontal section. The position of the upper end of the vertical section of the overflow weir (i.e., weir height) should be decided depending on the linear velocity of the culture broth passed from overflow exit 3 to cooler 5. The weir height can be reduced when the linear velocity is small.

The shape of the overflow weir in the transverse direction is arbitrary. For instance, it may be linear, as illustrated in FIG. 3, or may be round (overflow weir 2'), as in FIG. 4. Alternatively, the overflow weir 2 may be wave-shaped, square-shaped, or mixed shape. It is preferred to provide fermenter 1 with more than two coolers in the case where the overflow weir has a round shape, etc., as indicated in FIG. 4. The shape of the part where the overflow weir is set up at the inner wall of fermenter 1 may be varied and FIGS. 5-8 are examples thereof.

The provision of guide plate 4 between overflow weir 2 and overflow exit 3 as illustrated in FIG. 2 makes the separation of gas from liquid more efficient. The shape of the longitudinal section for the said guide plate is arbitrary. For example, it may be linear, as in FIG. 2, wave-shaped, or other arbitrary shapes. In the same way, the shape of the transverse section of guide plate 4 can be decided arbitrarily, and it may be linear, as in FIG. 9, round, as in FIG. 10, wave-shaped, square-shaped or mixed shape. The lower end of guide plate 4 is preferably provided so that it may be situated lower than the upper end of overflow exit 3.

The area, volume, etc., of the part where the overflow weir 2 and the guide plate 4 overlap each other should be properly decided taking into consideration factors such as the linear velocity of culture fluid, etc. Thus, a favorable result can be obtained.

By the use of the fermenter of the present invention, a very favorable cooling effect can be obtained because separation of gas and liquid is done rapidly from the culture broth introduced into the overflow weir, and the culture broth without bubbles is sent to a cooler 5 through the overflow exit 3. The separation of gas and liquid is further made smooth by providing a guide plate 4. In addition, the overflow weir occupies only an extremely small part of the fermenter and so the influence on efficient area for fermentation is slight. Furthermore, it is easy to provide a conventional fermenter with an overflow weir and a guide plate in accordance with the present invention, and there is no inconvenience in so modifying the fermenter because of their simple structure. Particularly, concurrent provision of the guide plate 4 makes further miniaturization possible.

Therefore, by cultivating microorganisms using the fermenter so equipped, bubble separation from a culture broth introduced to a cooler can be made advantageously, and thus fermentation can proceed favorably. The production of useful substances such as antibiotics, vitamins, amino acids, alcohols, organic acids, etc., and microbial cells can be done advantageously.

Typical examples involving use of the fermenter of the present invention are shown below.

EXAMPLE 1

A culture medium (700 liters) was placed in the fermenter (total length 2800 millimeters, diameter 700 millimeters) as illustrated in FIG. 1, provided with an overflow weir 480 millimeters in width and 270 millimeters in height with a linear-shaped transverse section (as in FIG. 3) at a point 170 millimeters below the lower end of the overflow exit and a distance of 100 millimeters from the inner wall. Seed culture (yeast: *Candida utilis*) obtained by cultivation was added to this culture medium and continuous cultivation was carried out under conditions of 32° C. and 1-3.5 VVM (3.0 - 11.0 centimeters/second) of ventilation volume.

The exit pipe extending from the fermenter 1 to the cooler 5 was made transparent for easy checking of the presence or absence of bubbles in the culture broth sent to the cooler 5 through overflow exit 3 to control the temperature during the culture process. As a result, it was observed that no bubbles were contained in the culture broth at the exit pipe except for a small amount in a few cases when the linear velocity of culture broth passed into the overflow weir was significantly large (more than 20 centimeters/second).

EXAMPLE 2

Yeast cells were produced in the same manner as in Example 1, except that a guide plate of 280 millimeters width and 350 millimeters height was provided at a distance 30 millimeters from the inner wall and a point 80 millimeters between the lower end of the overflow weir and the lower end of the guide plate as illustrated in FIG. 2.

As a result, no bubbles were contained in the culture broth at the exit pipe even when the linear velocity of the culture broth passed into the overflow weir was significantly large. The examination of the position of the lower end of the guide plate 4 indicated that a distance of from 20 to 130 millimeters from the bottom of the overflow weir 2 provides a favorable result in the case of this example.

What is claimed is:

1. In a stirred gas bubble fermenter having aeration means, a waste gas outlet and an overflow exit, and provided with a cooler outside the fermenter and coupled to the fermenter through said overflow exit,
  the improvement comprising:
  an overflow weir connected to the inner wall of the fermenter below said overflow exit and extending at least in the upward direction of the fermenter so as to be opposite at least a portion of said overflow exit; and
  a guide plate arranged between at least a portion of said overflow weir and at least a portion of said overflow exit to improve gas-liquid separation.

2. The fermenter according to claim 1, wherein the shape of the transverse section of said overflow weir is linear.

3. The fermenter according to claim 1, wherein the shape of the transverse section of said overflow weir is round.

4. The fermenter according to claim 1, wherein said overflow weir is generally, "L"-shaped in a vertical section, the horizontal leg thereof being connected to said inner wall of said fermenter below said overflow exit and the vertical leg thereof extending upwardly opposite said overflow exit.

5. The fermenter according to claim 4, wherein said vertical leg extends above the upper extremity of said overflow exit.

6. The fermenter according to claim 1, wherein said overflow weir comprises a member extending upwardly and inclined away from the inner wall of said fermenter.

7. The fermenter according to claim 6, wherein said upwardly extending member extends above the upper extremity of said overflow exit.

8. The fermenter according to claim 1, wherein said overflow weir extends above the upper extremity of said overflow exit.

9. The fermenter according to claim 1, wherein the shape of the transverse section of said guide plate is linear.

10. The fermenter according to claim 1, wherein the shape of the transverse section of said guide plate is round.

11. The fermenter according to claim 2, wherein the shape of the transverse section of said guide plate is linear.

12. The fermenter according to claim 3, wherein the shape of the transverse section of said guide plate is round.

13. The fermenter according to claim 1, wherein said guide plate extends below the lower extremity of said overflow exit.

14. The fermenter according to claim 13, wherein said guide plate extends above the upper extremity of said overflow weir.

15. The fermenter according to claim 14, wherein both said overflow weir and said guide plate extend above the upper extremity of said overflow exit.

16. The fermenter according to claim 1, wherein said guide plate extends above the upper extremity of said overflow weir.

17. The fermenter according to claim 16, wherein both said overflow weir and said guide plate extend above the upper extremity of said overflow exit.

18. The fermenter according to claim 1, wherein the lower end of said guide plate is situated lower than the upper extremity of said overflow exit.

19. The fermenter according to claim 1 wherein said guide plate cooperates with said overflow weir to define a tortuous path for the exit fluid from the fermenter.

* * * * *